(12) United States Patent
Ito

(10) Patent No.: US 12,171,899 B2
(45) Date of Patent: Dec. 24, 2024

(54) RADIATION STERILIZATION RESISTANT ADHESIVE

(71) Applicant: 3M INNOVATIVE PROPERTIES COMPANY, St. Paul, MN (US)

(72) Inventor: Takeshi Ito, Sagamihara (JP)

(73) Assignee: Solventum Intellectual Properties Company, Maplewood, MN (US)

( * ) Notice: Subject to any disclaimer, the term of this patent is extended or adjusted under 35 U.S.C. 154(b) by 699 days.

(21) Appl. No.: 17/418,731

(22) PCT Filed: Dec. 23, 2019

(86) PCT No.: PCT/IB2019/061317
§ 371 (c)(1),
(2) Date: Jun. 25, 2021

(87) PCT Pub. No.: WO2020/136572
PCT Pub. Date: Jul. 2, 2020

(65) Prior Publication Data
US 2022/0072194 A1   Mar. 10, 2022

(30) Foreign Application Priority Data
Dec. 27, 2018   (JP) ................. 2018-245837

(51) Int. Cl.
*A61L 24/04*   (2006.01)
*C09J 7/35*   (2018.01)
*C09J 133/10*   (2006.01)
*C09J 193/04*   (2006.01)

(52) U.S. Cl.
CPC ............ *A61L 24/043* (2013.01); *C09J 7/35* (2018.01); *C09J 133/10* (2013.01); *C09J 193/04* (2013.01); *C09J 2433/00* (2013.01); *C09J 2493/00* (2013.01)

(58) Field of Classification Search
CPC .......... A61L 24/04; C09J 7/35; C09J 193/04; C09J 133/10
USPC ........................................... 523/118
See application file for complete search history.

(56) References Cited

U.S. PATENT DOCUMENTS

| | | | | |
|---|---|---|---|---|
| 6,225,520 B1 * | 5/2001 | Bauduin | ............... | C09J 123/08 602/52 |
| 6,830,726 B2 | 12/2004 | Saito | | |
| 2002/0064670 A1 * | 5/2002 | Saito | ............... | C09J 7/385 428/480 |
| 2014/0302313 A1 * | 10/2014 | Suwa | ............... | C09J 133/14 525/289 |

FOREIGN PATENT DOCUMENTS

| | | | |
|---|---|---|---|
| JP | 59213783 | A | 12/1984 |
| JP | 2006043262 | | 2/2006 |
| JP | 2006045381 | | 2/2006 |
| JP | 2016-056296 | A | 4/2016 |
| WO | WO 1996-011992 | | 4/1996 |

OTHER PUBLICATIONS

International Search Report for PCT International Application No. PCT/IB2019/061317, mailed on Apr. 20, 2020, 5 pages.
Zhu, "Basic Coating Course", Chengdu, Southwest Jiaotong University Press, Jun. 2012, 7 pages.

* cited by examiner

*Primary Examiner* — Deve V Hall

(57) ABSTRACT

Provided is a radiation sterilization resistant adhesive agent layer capable of reducing or preventing a decrease in wettability of an adhesive after radiation sterilization treatment. The adhesive can be used with a medical implement, for example medical implements that are sterilized. The adhesive agent layer includes a (meth)acrylic polymer and a wettability stabilizer, and the wettability stabilizer is at least one selected from a rosin ester resin, a terpene phenol resin, and hydrides thereof.

13 Claims, 1 Drawing Sheet

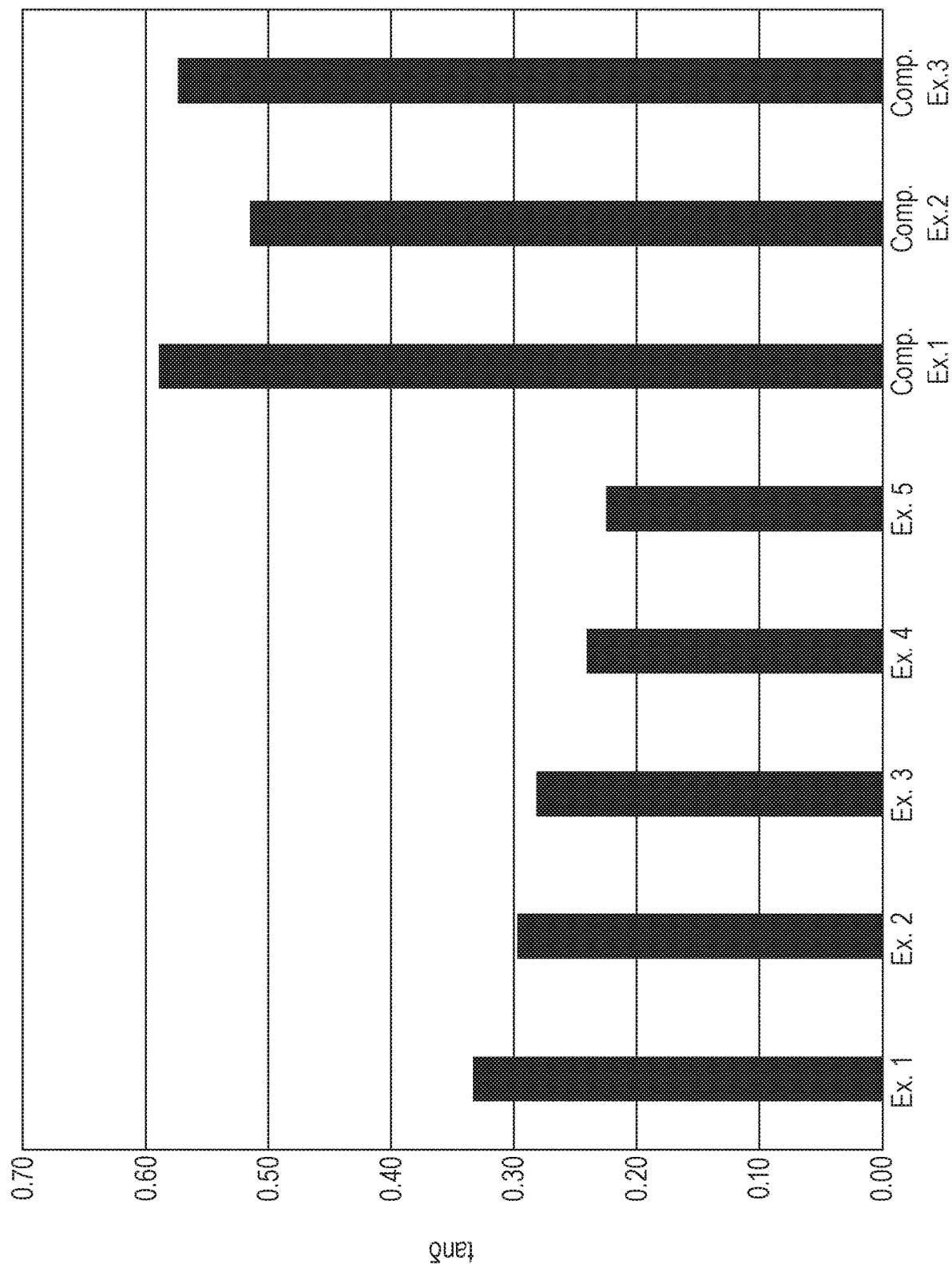

RADIATION STERILIZATION RESISTANT ADHESIVE

CROSS REFERENCE TO RELATED APPLICATIONS

This application is a national stage filing under 35 U.S.C. 371 of PCT/IB2019/061317 filed 23 Dec. 2019, which claims the benefit of Japanese Application No. 2018-245837, filed 27 Dec. 2018, the disclosures of each of which are incorporated by reference herein in their entireties.

TECHNICAL FIELD

The present disclosure relates to a radiation sterilization resistant adhesive. In particular, the adhesive can be used with medical member for skin application.

BACKGROUND ART

In recent years, various adhesives have been used in the medical field. The adhesives used in such a field may be subjected to sterilization treatment with radiation such as gamma rays and electron beams.

Patent Document 1 (JP 2002-114960 A; U.S. Pat. No. 6,830,726) discloses a radiation-resistant acrylic adhesive including a radiation-resistant agent and used for a packaging material and the like for medical equipment.

Patent Document 2 (JP 2006-043262 A) discloses an adhesive agent composition used in a bandage and the like, and including 100 parts by weight of a copolymer mainly including alkyl acrylate, and from 5 to 60 parts by weight of a first tackifier having a softening point of lower than 80° C. and viscosity at 50° C. of 10 Pa s or less, and from 5 to 60 parts by weight of a second tackifier having a softening point of 80 to 150° C.

SUMMARY

The wettability of an adhesive is closely related to changes over time in adhesive properties such as adhesive force to skin, and thus is very important as a property of a bonding agent intended for use for skin.

Appropriate wettability design can achieve desired adhesive properties, while inappropriate wettability such as over-spreading induces damage to skin due to an excessive increase in adhesive force, and insufficient wettability induces dropout of a medical member.

It is very important to design and maintain appropriate wettability, and this cannot be discussed by initial adhesive force alone.

On the other hand, when an adhesive including an acrylic polymer or the like is subjected to sterilization treatment with radiation such as gamma rays and electron beams, crosslinking density increases, and wettability may reduce. When such an adhesive is used in a medical member to be subjected to sterilization treatment with radiation, the adhesive cannot sufficiently achieve intended performance, and thus the adhesive cannot be used, for example, as an adhesive for a medical member including a medical implement such as testing equipment for testing a blood glucose level or the like over a long period of time.

The present disclosure provides a radiation sterilization resistant adhesive agent layer capable of reducing or preventing a decrease in the wettability of an adhesive after radiation sterilization treatment. Such radiation sterilization resistant adhesive agent can be used with a medical implement.

In one embodiment of the present disclosure, provided is a medical member for skin application including a medical implement and an adhesive agent layer resistant to radiation sterilization, the adhesive agent layer including a (meth) acrylic polymer and a wettability stabilizer, and the wettability stabilizer is selected from a rosin ester resin, a terpene phenol resin, and hydrides thereof.

In the present disclosure, a medical member for skin application including a radiation sterilization resistant adhesive agent layer reduces prevents a decrease in wettability of an adhesive after radiation sterilization treatment, and a medical implement can be provided.

The above description is not be construed that all embodiments of the present invention and all advantages of the present invention are disclosed.

BRIEF DESCRIPTION OF DRAWINGS

FIG. 1 is a graph of an absolute value obtained by subtracting a loss tangent tan δ at 90° C. of an adhesive after radiation sterilization treatment from a loss tangent tan δ at 90° C. of the adhesive before radiation sterilization treatment.

DESCRIPTION OF EMBODIMENTS

A medical member for skin application in a first embodiment of the present disclosure includes a medical implement such as a backing, dosing equipment, communication equipment, testing equipment, and protective equipment, and an adhesive agent layer resistant to radiation sterilization, the adhesive agent layer including a (meth)acrylic polymer and a wettability stabilizer, and the wettability stabilizer being at least one selected from a rosin ester resin, a terpene phenol resin, and hydrides thereof. Such an adhesive agent layer is capable of reducing or preventing a decrease in performance such as wettability after radiation sterilization treatment, and thus even when the medical member for skin application is subjected to radiation sterilization treatment, the adhesive agent layer can appropriately wet and spread in an uneven surface such as skin and can sufficiently hold the medical member.

As the wettability stabilizer of the adhesive agent layer in the medical member of the first embodiment, at least one selected from a terpene phenol resin and a hydride thereof can be used. The adhesive agent layer including such a wettability stabilizer exhibits appropriate wettability, and also has excellent performance such as crosslinkability and adhesiveness.

A blending amount of the wettability stabilizer in the adhesive agent layer of the medical member of the first embodiment may be from about 15 to about 60 mass %. The adhesive agent layer including a predetermined amount of the wettability stabilizer can further reduce or prevent decrease in performance such as wettability.

The adhesive agent layer of the medical member of the first embodiment can be of a hot melt type. The adhesive agent layer may not include a solvent, and thus can be used suitably for skin, as compared to a solvent-based adhesive or the like.

The thickness of the adhesive agent layer of the medical member of the first embodiment may be from about 10 to about 300 μm. The adhesive agent layer having such a thickness can appropriately wet and spread in unevenness of skin, and thus can improve the holding performance of the medical member.

As the medical implement of the medical member of the first embodiment, at least one selected from a backing, dosing equipment, communication equipment, testing equipment, and protective equipment can be used. For example, a backing can be a paper, film, foam, nonwoven, foil, single layer or multilayer.

Detailed description will be given for the purpose of exemplifying representative embodiments of the present invention, but the present invention is not limited to these embodiments.

In the present disclosure, "(meth)acrylate" means acrylate or methacrylate, and "(meth)acrylic" means acrylic or methacrylic, and "(meth)acryloyl" means "acryloyl" or "methacryloyl."

In the present disclosure, a "(meth)acrylate polymer" can also include a polymer of a concept commonly referred to as a "(meth)acrylate copolymer."

In the present disclosure, "crosslinking" can also include a concept commonly referred to as "curing."

In the present disclosure, a "UV crosslinkable site" refers to a site that is activated by UV irradiation to form a crosslink between a (meth)acrylic polymer and other portion within a molecule of a (meth)acrylic polymer including a UV crosslinkable site, or between a (meth)acrylic polymer and other molecules of a (meth)acrylic polymer including a UV crosslinkable site.

In the present disclosure, the term "alkyl" means a linear or branched aliphatic hydrocarbon group. In the present disclosure, the term "branched" means that one or more alkyl groups such as methyl, ethyl or propyl are bonded to a linear alkyl chain. The alkyl group may be unsubstituted or substituted with one or more halo atoms, cycloalkyl, or cycloalkenyl groups.

In the present disclosure, the term "cycloalkyl" means a non-aromatic monocyclic or polycyclic ring system, and includes, for example, from about 3 to about 12 carbon atoms. Examples of the cycloalkyl ring include cyclopentyl, cyclohexyl, and cycloheptyl. This cycloalkyl group may be substituted with one or more halo atoms, methylene, alkyl, cycloalkyl, heterocyclyl, aralkyl, heteroaralkyl, aryl, or heteroaryl. In the present disclosure, the term "hetero" means oxygen, nitrogen, or sulfur substituted with one or more carbon atoms.

In the present disclosure, the term "cycloalkenyl" means a non-aromatic monocyclic or polycyclic ring system including a carbon-carbon double bond, and includes, for example, from about 3 to about 10 carbon atoms. The cycloalkenyl group may be unsubstituted and substituted with one or more halo atoms, methylene, alkyl, cycloalkyl, heterocyclyl, aralkyl, heteroaralkyl, aryl, or heteroaryl groups.

In the present disclosure, the term "aryl" means an aromatic carbocyclic radical. Examples of the aryl group include phenyl or naphthyl substituted with one or more aryl group substituents, which may be identical or different. Here, examples of the "aryl group substituent" include hydrogen, alkyl, cycloalkyl, optionally substituted aryl, optionally substituted heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, carboxy, acyl, aroyl, halo, nitro, cyano, carboxy, alkoxycarbonyl, aryloxycarbonyl, aralcoxy carbonyl, acylamino, aroylamino, alkylsulfonyl, arylsulfonyl, and other known groups.

The description of the chemical groups listed above is known in the art, and the description of these is not intended to change the meaning generally accepted.

Hereinafter, a medical member for skin application (may simply be referred to as a "medical member") will further be described below.

The medical member of the present disclosure includes a medical implement such as dosing equipment, communication equipment, testing equipment, and protective equipment, and a radiation sterilization resistant adhesive agent layer (may be referred to simply as an "adhesive agent layer"). Such an adhesive agent layer includes a (meth) acrylic polymer and a specific wettability stabilizer, and thus can exhibit appropriate wettability even after radiation sterilization treatment. As a result, an adhesive can appropriately wet and spread even in an uneven surface such as skin, and thus the medical member including various medical implements can be bonded stably to skin over a long period of time.

In this manner, the medical member of the present disclosure can be used in a state where the medical member is stably applied to skin for a relatively long period of time (e.g., a period of one day or two days or more). Specifically, the medical member of the present disclosure can be used for example, in the case of appropriately monitoring a patient's health condition and dosing, and thus the medical member is capable of reducing or preventing a risk that a physical condition and health management of a patient be affected by unintentional detachment of the medical member.

Additionally, the medical member includes a relatively expensive medical implement such as testing equipment, and thus cannot be replaced frequently.

Therefore, the adhesive agent layer of the present disclosure that exhibits not only short-term adhesive force but also appropriate wettability and can stably exhibit good adhesive force and the like for a long period of time is regarded as a particularly preferable material as an adhesive agent layer of a medical member for skin application.

Here, the wettability of the adhesive agent layer cannot be evaluated only by initial adhesive force (adhesive strength) with respect to a flat PP plate or the like, which can vary depending on, for example, the type of an adherend, a peeling angle and peeling speed of a cohesive tape, the type of a substrate of a cohesive tape, and the thickness of the adhesive agent layer as disclosed in Patent Document 1. The wettability of the adhesive agent layer can be evaluated by, for example, a loss tangent tan $\delta$ of an adhesive alone constituting the adhesive agent layer. The loss tangent tan $\delta$ is a numerical value represented by a ratio of viscosity of the adhesive itself (wetting and spreading property of the adhesive) to elasticity (cohesiveness of the adhesive) and is an important parameter by which good balance between viscosity and elasticity can be confirmed. The loss tangent tan $\delta$ can be determined, for example, by a dynamic viscoelasticity test described below.

Specifically, the loss tangent tan $\gamma$, particularly the loss tangent tan $\delta$ at 90° C. of the adhesive of the present disclosure can be define as, for example, 0.80 or more, 0.90 or more, or 1.00 or more, and can be defined as 1.80 or less, 1.70 or less, or 1.60 or less before radiation sterilization treatment.

The adhesive having the loss tangent tan $\delta$ in such a range can exhibit appropriate wettability and cohesiveness, and thus the adhesive can spread appropriately in an uneven adherend such as skin and exhibit good adhesive force.

The adhesive of the present disclosure is capable of reducing or preventing fluctuation in the loss tangent tan $\delta$ even after radiation sterilization treatment. Specifically, the adhesive of the present disclosure can satisfy, for example, conditions of Formula 1 below:

$$|X-Y| \leq \text{about } 0.45 \qquad \text{Formula 1}$$

In the formula, X is the loss tangent tan δ of the adhesive at 90° C. before radiation sterilization treatment, and Y is the loss tangent tan δ of the adhesive at 90° C. after radiation sterilization treatment.

It can be intended that the smaller a value of |X−Y|, the less change (denaturation) in wettability, cohesiveness, and the like between the adhesive before radiation sterilization treatment and the adhesive after radiation sterilization treatment. In the adhesive of the present disclosure, the value of |X−Y| can be about 0.45 or less, about 0.40 or less, about 0.35 or less, or about 0.30 or less. A lower limit of the value of |X−Y| is not particularly limited, but can be defined as, for example, about 0.00 or greater, about 0.05 or greater, or about 0.10 or greater.

The adhesive agent layer of the present disclosure includes a (meth)acrylate polymer. This (meth)acrylate polymer is a polymer different from, for example, a (meth) acrylic polymer including a UV crosslinkable site described below, and can be obtained by, for example, polymerizing a monomer component including a monofunctional monomer and optionally a polyfunctional (meth)acrylate.

Examples of the monofunctional monomer can include an alkyl (meth)acrylate having from 1 to 20 carbon atoms in an alkyl group (may be referred to as "C1 to 20 alkyl (meth) acrylate"), and an unsaturated monomer including a vinylcarbonyl group and a polar group (may be referred to as a "polar unsaturated monomer"). The monofunctional monomer can be used alone, or in combination of two or more thereof, and may include a UV crosslinkable site.

The "alkyl (meth)acrylate having from 1 to 20 carbon atoms in an alkyl group" means that, for example, alkyl alcohol has from 1 to 20 carbon atoms when the alkyl (meth)acrylate is considered as an ester of an acrylic acid and alkyl alcohol. That is, when the alkyl (meth)acrylate is represented as $CH_2=CH-COO-R^1$, $R^1$ means an alkyl group having from 1 to 20 carbon atoms.

The alkyl group of the alkyl (meth)acrylate has, for example, from the perspective of adhesive force or adhesion force of the adhesive, preferably from 4 to 12 carbon atoms, and from the perspective of wettability of the adhesive and gentle application to skin, preferably from 8 to 18 carbon atoms. In this manner, the number of carbon atoms in the alkyl group of the alkyl (meth)acrylate can be selected as appropriate according to the use and application of the medical member.

Examples of the alkyl (meth)acrylate include methyl (meth)acrylate, ethyl (meth)acrylate, n-propyl (meth)acrylate, isopropyl (meth)acrylate, n-butyl (meth)acrylate, isobutyl (meth)acrylate, sec-butyl (meth)acrylate, tert-butyl (meth)acrylate, n-pentyl (meth)acrylate, n-hexyl (meth) acrylate, 2-ethylhexyl (meth)acrylate, n-heptyl (meth)acrylate, n-octyl (meth)acrylate, isooctyl (meth)acrylate, n-nonyl (meth)acrylate, isononyl (meth)acrylate, n-decyl (meth) acrylate, n-undecyl (meth)acrylate, n-dodecyl (meth)acrylate, n-tridecyl (meth)acrylate, n-tetradecyl (meth)acrylate, n-pentadecyl (meth)acrylate, n-hexadecyl (meth)acrylate, n-heptadecyl (meth)acrylate, n-octadecyl (meth)acrylate, cyclohexyl (meth)acrylate, 3,3,5-trimethylcyclohexyl (meth)acrylate, and isobornyl (meth)acrylate. Among these, 2-ethylhexyl (meth)acrylate is preferable from the perspective of wettability, adhesiveness, resistance to radiation such as electron beams, and usability with respect to skin.

The polar unsaturated monomer has a vinylcarbonyl group and a polar group.

Examples of the polar group include a hydroxyl group, a carboxyl group, a carbamoyl group, an amino group, an epoxy group, and a nitrile group. Among them, a hydroxyl group, a carboxyl group, and an amino group are preferable.

The vinylcarbonyl group refers to a group represented by $CH_2=CH-C(=O)-$. The vinylcarbonyl group and the polar group may be bonded directly or may be bonded via a linking group such as an alkylene group.

Examples of the polar unsaturated monomer include:
a hydroxyl group-containing unsaturated monomer such as 2-hydroxyethyl (meth)acrylate, 3-hydroxypropyl (meth)acrylate, 4-hydroxybutyl (meth)acrylate, polyethylene glycol (meth)acrylate, and polypropylene glycol (meth)acrylate;
a carboxyl group-containing unsaturated monomer such as acrylic acid, itaconic acid, maleic acid, and fumaric acid (may be referred to simply as "carboxylic acid");
a carbamoyl group-containing unsaturated monomer such as acrylamide;
an amino group-containing monomer such as N,N-dimethylaminoethyl (meth)acrylate, N,N-diethylaminoethyl (meth)acrylate, and N,N-dimethylaminopropyl (meth)acrylate; and
an epoxy group-containing unsaturated monomer such as glycidyl (meth)acrylate.

Examples of the polyfunctional (meth)acrylate that is an optional component include 1,6-hexanediol di(meth)acrylate, 1,9-nonanediol di(meth)acrylate, ethylene glycol di(meth)acrylate, polyethylene glycol di(meth)acrylate, propylene glycol di(meth)acrylate, polypropylene glycol di(meth)acrylate, neopentyl glycol di(meth)acrylate, pentaerythritol di(meth)acrylate, pentaerythritol tri(meth)acrylate, dipentaerythritol hexa(meth)acrylate, trimethylolpropane tri (meth)acrylate, and tetramethylol methane tri(meth)acrylate.

The (meth)acrylate polymer can be prepared by using a known polymerization method such as solution polymerization, emulsion polymerization, suspension polymerization, bulk polymerization, photopolymerization, and solventless polymerization.

In a case where a polar unsaturated monomer such as carboxylic acid is used in the preparation of the (meth) acrylate polymer, the polar unsaturated monomer can be mixed by about 1.0 mass % or more, about 1.5 mass % or more, or about 2.0 mass % or more, and can be mixed by about 20.0 mass % or less, about 15.0 mass % or less, or about 10.0 mass % or less per 100 mass % of the total amount of the (meth)acrylate monomer and the carboxylic acid. When the content of the polar unsaturated monomer is in such a range, adhesiveness of the adhesive can be improved. Here, the "(meth)acrylate monomer" can be intended to mean a monomer component of the (meth) acrylate other than a polar unsaturated monomer among the monomer components of the (meth)acrylate polymer.

The weight average molecular weight of the (meth) acrylate polymer of the present disclosure is not particularly limited, and can be defined as, for example, about 100000 or greater, about 200000 or greater, or about 300000 or greater, and can be defined as about 1.5 million or less, about 1 million or less, or about 800000 or less. When the weight average molecular weight is within this range, appropriate cohesive strength and good adhesive force can be imparted to the adhesive. The "weight average molecular weight" in the present disclosure means a molecular weight in terms of standard polystyrene by the GPC method.

The adhesive agent layer of the present disclosure includes at least one wettability stabilizer selected from a rosin ester resin, a terpene phenol resin, and hydrides thereof. The adhesive agent layer including these wettability stabilizers is capable of reducing or preventing denaturation of wettability and the like of the adhesive, even after application of radiation sterilization treatment with electron beams or the like. Namely, the adhesive of the adhesive agent layer of the present disclosure is capable of reducing or preventing denaturation of wettability and the like due to radiation sterilization treatment applied to the medical member, and thus initial design such as adhesive force and the like of the adhesive according to required performance can be controlled freely.

Among the above-described wettability stabilizers, from the perspective of adhesiveness, crosslinkability, and the like, at least one selected from a terpene phenol resin and a hydride thereof is preferable.

The adhesive agent layer of the present disclosure includes a (meth)acrylic polymer and a wettability stabilizer. A blending amount of the wettability stabilizer in the adhesive agent layer is not particularly limited, but can be, for example, about 15 mass % or greater, about 16 mass % or greater, or about 17 mass % or greater, and can be about 60 mass % or less, about 55 mass % or less, about 50 mass % or less, about 45 mass % or less, about 40 mass % or less, about 38 mass % or less, 35 mass % or less, or 30 mass % or less. When the content of the wettability stabilizer is in this range, denaturation of wettability and the like of the adhesive after radiation sterilization treatment can further be reduced or prevented.

The adhesive agent layer of the present disclosure includes a composition including a (meth)acrylic polymer, a wettability stabilizer, and a crosslinking agent, and can be prepared by using the composition. The use of the composition including a crosslinking agent can impart a crosslinked structure to the adhesive agent layer. The crosslinking agent is not particularly limited, and for example, a thermal crosslinking agent or a UV crosslinking agent can be used, but a UV crosslinking agent is preferably from the perspective of productivity and the like.

Examples of the thermal crosslinking agent can include an isocyanate compound such as hexamethylene diisocyanate and toluidine diisocyanate; an epoxy compound such as 1,3-bis (N,N-diglycidylaminomethyl) toluene and N,N,N',N'-tetraglycidyl-4,4'-diaminodiphenylmethane; a metal chelate compound such as trisethyl acetoacetate aluminum and ethyl acetoacetate aluminum diisopropylate; and an imine compound such as N,N'-toluene-2,4-bis (1-aziridinecarboxamide) triethylenemelamine and hexamethylenediethyleneurea. These can be used alone or in combination of two or more thereof.

As the UV crosslinking agent, for example, at least one of a benzophenone compound such as benzophenone, benzoylbenzoic acid, methyl benzoylbenzoate, 4-phenylbenzophenone, hydroxybenzophenone, 4-benzoyl-4'-methyldiphenyl sulfide, and 3,3'-dimethyl-4-methoxybenzophenone, and a (meth)acrylic polymer including a UV crosslinkable site can be used.

The (meth)acrylic polymer including a UV crosslinkable site can act as an additive to render a composition including a (meth)acrylic polymer and a wettability stabilizer to be UV crosslinkable. A composition including such a (meth)acrylic polymer including a UV crosslinkable site has good compatibility with other components and is less likely to cause microscopic or macroscopic phase separation, and thus can improve performance such as crosslinkability and transparency. The UV crosslinkable site may be a polymerizable functional group such as a (meth)acryl group and an epoxy group and may include a structure capable of extracting a hydrogen radical by UV irradiation.

The (meth)acrylic polymer including a UV crosslinkable site of the representative embodiment includes at least one type of structure capable of extracting a hydrogen radical by UV irradiation. This structure is excited by UV irradiation to extract a hydrogen radical from a (meth)acrylic polymer and other portions within a molecule of a (meth)acrylic polymer including a UV crosslinkable site, or a (meth)acrylic polymer and other molecules of a (meth)acrylic polymer including a UV crosslinkable site in the adhesive agent composition. As a result, a radical is generated on the molecules of the (meth)acrylic polymer and the (meth)acrylic polymer including a UV crosslinkable site, and various kinds of reaction such as formation of a crosslinked structure by bonding of the generated radical, generation of a peroxide radical by reaction with an oxygen molecule, formation of a crosslinked structure via the generated peroxide radical, extraction of another hydrogen radical by the generated radical occur in the system, and finally the adhesive agent composition of the present disclosure is crosslinked to obtain an adhesive. Since no additional photoinitiator is required, it is advantageous that the UV crosslinkable site includes a structure capable of extracting a hydrogen radical by UV irradiation.

Examples of the structure capable of extracting a hydrogen radical by UV irradiation can include a benzophenone group, a benzyl group, an o-benzoylbenzoate group, a thioxanthone group, a 3-ketocoumarin group, a 2-ethylanthraquinone group, and a camphor quinone group. Among these, a benzophenone group is preferably used from the perspective of transparency, reactivity, and the like.

The (meth)acrylic polymer including the structure capable of extracting a hydrogen radical by UV irradiation may be a copolymer of at least one alkyl (meth)acrylate selected from an alkyl (meth)acrylate including a linear, branched or cyclic alkyl group having from 1 to 22 carbon atoms and a (meth)acrylate including, for example, a benzophenone group, a benzyl group, an o-benzoylbenzoate group, a thioxanthone group, a 3-ketocoumarin group, a 2-ethylanthraquinone group, or a camphor quinone group.

Usable examples of the (meth)acrylate including a benzophenone group include 4-acryloyloxybenzophenone, 4-acryloyloxyethoxybenzophenone, 4-acryloyloxy-4'-methoxybenzophenone, 4-acryloyloxyethoxy-4'-methoxybenzophenone, 4-acryloyloxy-4'-bromobenzophenone, 4-acryloyl oxyethoxy-4'-bromobenzophenone, 4-methacryloyloxybenzophenone, 4-methacryloyloxyethoxybenzophenone, 4-methacryloyloxy-4'-methoxybenzophenone, 4-methacryloyloxyethoxy-4'-methoxybenzophenone, 4-methacryloyloxy-4'-bromobenzophenone, 4-methacryloyloxyethoxy-4'-bromobenzophenone, and mixtures thereof. Among these, from the perspective of achieving excellent balance between stability and reactivity, a (meth)acrylate including an alkylene group such as an alkylene group having from 1 to 6 carbon atoms between a (meth)acryloyl group and a benzophenone group is advantageous, and examples of such a (meth)acrylate include 4-acryloyloxyethoxybenzophenone, 4-acryloyloxyethoxy-4'-methoxybenzophenone, 4-acryloyloxyethoxy-4'-bromobenzophenone, 4-methacryloyloxyethoxybenzophenone, 4-methacryloyloxyethoxy-4'-methoxybenzophenone, and 4-methacryloyloxyethoxy-4'-bromobenzophenone.

Examples of the alkyl (meth)acrylate including a linear, branched or cyclic alkyl group having from 1 to 22 carbon atoms include methyl (meth)acrylate, ethyl (meth)acrylate, n-butyl (meth)acrylate, hexyl (meth)acrylate, n-octyl (meth)acrylate, 2-ethylhexyl (meth)acrylate, isobutyl (meth)acrylate, tert-butyl (meth)acrylate, cyclohexyl (meth)acrylate, isobornyl (meth)acrylate, and dicyclopentanyl (meth)acrylate.

In some embodiments, in the structure capable of extracting a hydrogen radical by UV irradiation, for example, the number of moles of a benzophenone group can be about 0.3 $\mu$mol/g or more, about 5 $\mu$mol/g or more, or about 10 $\mu$mol/g or more, and can be about 320 $\mu$mol/g or less, about 250 $\mu$mol/g or less, or about 150 $\mu$mol/g or less based on the total mass of the (meth)acrylic polymer and the (meth)acrylic polymer including a UV crosslinkable site in the composition. An amount of the structure capable of extracting a hydrogen radical by UV irradiation is set to be within this range, and thus density of a crosslinked structure formed by UV irradiation can be controlled to adjust performance such as adhesiveness.

The (meth)acrylic polymer including a UV crosslinkable site may include one or more of polymerized units derived from monomers other than those described above. Examples of such other monomers include an olefin such as ethylene, butadiene, isoprene, and isobutylene; a vinyl monomer such as vinyl acetate, vinyl propionate and styrene; a hydroxyl group-containing monomer such as 2-hydroxyethyl (meth)acrylate, 2-hydroxypropyl (meth)acrylate, 3-hydroxypropyl (meth)acrylate, 2-hydroxybutyl (meth)acrylate, 4-hydroxybutyl (meth)acrylate, 1,4-cyclohexanedimethanol mono (meth)acrylate, 1-glycerol (meth)acrylate, 2-hydroxyethyl (meth)acrylamide, N-hydroxypropyl (meth)acrylamide, vinyl alcohol, and allyl alcohol; a carboxyl group-containing monomer such as (meth)acrylic acid, itaconic acid, maleic acid, fumaric acid, crotonic acid, and isocrotonic acid or an anhydride thereof (e.g., maleic anhydride); an amide group-containing monomer such as N-vinylcaprolactam, N-vinylpyrrolidone, (meth)acrylamide, N-methyl (meth)acrylamide, N, N-dimethyl (meth)acrylamide, and N-octyl (meth)acrylamide; and an amino group-containing monomer such as N, N-dimethylaminoethyl (meth)acrylate, N, N-diethylaminoethyl (meth)acrylate, and N, N-dimethylaminoethyl (meth)acrylamide.

The (meth)acrylic polymer including a UV crosslinkable site can be produced by polymerizing the monomer described above in the presence of a polymerization initiator. A polymerization method may be a common radical polymerization method such as solution polymerization, emulsion polymerization, suspension polymerization, or bulk polymerization.

To prevent reaction of the UV crosslinkable site, radical polymerization with a thermal polymerization initiator is preferably used. Examples of such a thermal polymerization initiator include an organic peroxide such as benzoyl peroxide, t-butyl perbenzoate, cumene hydroperoxide, diisopropyl peroxydicarbonate, di-n-propyl peroxydicarbonate, di(2-ethoxyethyl) peroxydicarbonate, t-butylperoxyneodecanoate, t-butyl peroxypivalate, lauroyl peroxide, (3,5,5-trimethylhexanoyl) peroxide, dipropionyl peroxide, and diacetyl peroxide; and an azo compound such as 2,2'-azobisisobutyronitrile, 2,2'-azobis (2-methylbutyronitrile), 1,1'-azobis (cyclohexane-1-carbonitrile), 2,2'-azobis (2,4-dimethylvaleronitrile), 2,2'-azobis (2,4-dimethyl-4-methoxyvaleronitrile), dimethyl-2,2'-azobis (2-methylpropionate), 4,4'-azobis (4-cyanovaleric acid), 2,2'-azobis (2-hydroxymethylpropionitrile), and 2,2'-azobis [2-(2-imidazolin-2-yl)propane].

The weight average molecular weight of the (meth)acrylic polymer including a UV crosslinkable site is not particularly limited, and can be defined as, for example, about 10000 or greater, about 50000 or greater, or about 100000 or greater, and can be defined as about 1 million or less, about 800000 or less, or about 600000 or less.

A blending amount of the crosslinking agent in the composition (adhesive agent composition) for preparing the adhesive agent layer is not particularly limited, but can be, for example, about 0.05 mass % or greater, about 0.1 mass % or greater, about 0.5 mass % or greater, or about 1.0 mass % or greater, and about 10 mass % or less, about 5.0 mass % or less, or about 1.0 mass % or less in terms of solid content. When the content of the crosslinking agent is in this range, denaturation of wettability and the like of the adhesive after radiation sterilization treatment can further be reduced or prevented.

The adhesive agent composition can be blended with one or more of other optional components within the range that does not affect the effects of the present disclosure. Examples of the other components include a thermoplastic resin other than a (meth)acrylic polymer, a filler, a conductive agent, a thermally conductive agent, an antioxidant, a ultraviolet absorber, a photostabilizer, a thermal stabilizer, a dispersant, a plasticizer, a lubricant, a surfactant, a leveling agent, a silane coupling agent, a catalyst, a pigment, and a dye.

The adhesive agent layer of the present disclosure can be obtained by, for example, applying a composition including a (meth)acrylic polymer, a wettability stabilizer, and a crosslinking agent to a substrate or a release liner described below, and then performing heating treatment or UV irradiation treatment.

The heating treatment can also be performed by using, for example, a heater such as an infrared heater, hot air, an oven, or the like. The heating treatment can be performed in batch or can be performed continuously by using a belt conveyor or the like, but from the perspective of productivity and the like, the heating treatment is preferably performed continuously. A heating temperature (set temperature) can be, for example, about 70° C. or higher, about 80° C. or higher, or about 90° C. or higher. An upper limit of the heating temperature is not particularly limited, but can be defined as, for example, about 160° C. or lower, about 140° C. or lower, or about 120° C. or lower.

UV irradiation can be performed by using a light source such as a low-pressure mercury lamp, a medium pressure mercury lamp, a high-pressure mercury lamp, an ultrahigh pressure mercury lamp, a xenon lamp, a metal halide lamp, an electrode free lamp, or UV-LED. The UV irradiation can be performed in batch or can be performed continuously by using a belt conveyor or the like, but from the perspective of productivity and the like, the UV irradiation is preferably performed continuously. An amount of UV irradiation (UV-C) can be defined as, for example, about 1 mJ/cm$^2$ or greater, about 50 mJ/cm$^2$ or greater, or about 100 mJ/cm$^2$ or greater. An upper limit value of the amount of UV irradiation is not particularly limited, but can be defined as, for example, about 500 mJ/cm$^2$ or less or about 450 mJ/cm$^2$ or less.

As the adhesive agent layer of the present disclosure, an adhesive agent layer of a hot melt type can be used. Such an adhesive agent layer may be free of solvent, and thus can be used suitably for skin, as compared to a solvent-type adhesive or the like and can reduce the generation of a volatile organic compound (VOC) in a production step, and thus is desirable from the perspective of environmental conservation.

The thickness of the adhesive agent layer of the present disclosure may be selected appropriately in consideration of, for example, wettability to skin and required adhesive force, and can be, for example, but not limited to, about 10 μm or greater, about 20 μm or greater, or about 30 μm or greater, and can be about 300 μm or less, about 200 μm or less, or about 100 μm or less. The adhesive agent layer having such a thickness can appropriately wet and spread in unevenness of skin, and thus can improve the holding performance of the medical member.

In the adhesive agent layer of the present disclosure, an adhesive constituting the layer can exhibit performance related to the loss tangent tan δ that is a guideline for the wettability and cohesiveness described above, and can reduce or prevent glue residue, or can exhibit adhesion performance as described below.

In the adhesive agent layer of the present disclosure, in a 180 degree peel test, the adhesive force of the adhesive agent layer with respect to a polypropylene plate (for example, adhesive force within about two minutes after application of an adhesive) can be, for example, about 1.0 N/inch or greater, about 2.0 N/inch or greater, or about 3.0 N/inch or greater, and can be about 35 N/inch or less, about 20 N/inch or less, or about 15 N/inch or less before radiation sterilization treatment, and can be about 1.0 N/inch or greater, about 2.0 N/inch or greater, or about 3.0 N/inch or greater, and can be about 20 N/inch or less, about 17 N/inch or less, or about 15 N/inch or less after radiation sterilization treatment.

Alternatively, for example, the adhesive force of the adhesive agent layer with respect to artificial leather (e.g., adhesive force within about 2 minutes after application of an adhesive) can be about 1.0 N/inch or greater, about 2.0 N/inch or greater, or about 3.0 N/inch or greater, and can be about 25 N/inch or less, about 20 N/inch or less, or about 15 N/inch or less before radiation sterilization treatment, and can be about 1.0 N/inch or greater, about 2.0 N/inch or greater, or about 3.0 N/inch or greater, and can be about 20 N/inch or less, about 15 N/inch or less, or about 10 N/inch or less after radiation sterilization treatment.

When the adhesive force of the adhesive before radiation sterilization treatment is a (N/inch) and the adhesive force of the adhesive after radiation sterilization treatment is b (N/inch), the adhesive can satisfy Formula 2 below in a 180 degree peel test:

$$|a-b| \leq \text{about } 8.0 \, N/\text{inch} \qquad \text{Formula 2}$$

A value of |a−b| of such an adhesive can further be defined as about 7.0 N/inch or less, about 5.0 N/inch or less, about 3.0 N/inch or less, about 2.5 N/inch or less, about 2.0 N/inch or less, or about 1.5 N/inch or less. A lower limit of the value of |a−b| is not particularly limited, but can be defined as, for example, about 0 N/inch or more, or about more than about 0 N/inch.

The adhesive agent layer of the present disclosure is applied to the medical member of the present disclosure together with a medical implement. The adhesive agent layer may be applied directly to a medical implement or may be applied to a medical implement via a substrate. When the adhesive agent layer is applied to a medical implement via a substrate, the configuration can be, for example, a medical implement/an adhesive agent layer/a substrate/an adhesive agent layer, or a medical implement/a bonding agent layer/a substrate/an adhesive agent layer. A release liner may be applied to a surface of the adhesive agent layer opposite to the medical implement side. In the adhesive agent layer, the substrate, the bonding agent layer, and the like, a pore that can provide breathability may be formed appropriately.

The medical implement applied to the medical member of the present disclosure is not particularly limited, and examples of the medical implement can include at least one selected from dosing equipment, communication equipment, testing equipment, and protective equipment.

Examples of the dosing equipment can include equipment capable of administering various drugs such as insulin in the form of infusion or the like by a predetermined amount and/or for a predetermined period.

Examples of the communication equipment can include equipment capable of transmitting and receiving information to dosing equipment, testing equipment and the like, and/or information from such equipment, through wireless means such as Wi-Fi or wired means.

Examples of the testing equipment can include equipment for measuring at least one biological signal selected from blood, heartbeat, a pulse, a brainwave, blood pressure, and respiration. As for blood measurement, examples of an item that can be tested in a blood test can include at least one of a red blood cell count, hemoglobin, hematocrit, a white blood cell count, a platelet count, serum calcium, MCV, MCH, MCHC, total cholesterol, HDL cholesterol, LDL cholesterol, neutral fat, a blood glucose level, $HbA_{1c}$, urine sugar, uric acid, ZTT, AST, ALT, γ-GTP, ALP, total bilirubin, urinary urobilinogen, total protein, albumin, an Hbs antigen, an Hbs antibody, an HCV antibody, amylase, CRP, and a rheumatoid factor.

Examples of the protective equipment can include a member used in a surgical drape for protecting against sagging of antiseptic solution during surgery, blood adhesion, and the like. As such a member, for example, the same one as the following substrate can be used alone or in combination of two or more thereof.

The medical member of the present disclosure can be provided as appropriate, for example, by optionally using a substrate that supports an adhesive agent layer, a bonding agent layer that connects a medical implement and the substrate, and a release liner that protects the adhesive agent layer, alone or in combination of two or more thereof. The use of such a member enables improvement of performance such as productivity, strength, and storage properties.

In the present disclosure, the substrate is a member that, unlike the release member, is not intended to be peeled away, and can be intended to be a member capable of supporting the adhesive agent layer. A material of such a substrate is not particularly limited, and examples of the material can include a resin material such as polyolefin such as polyethylene, and polypropylene, and polyester such as PET; a rubber material; an inorganic material such as glass and ceramics; and a paper material. These can be used alone or in combination of two or more thereof. Among these, a resin material is preferable from the perspective of productivity and the like.

A shape or a form of the substrate is not particularly limited, and may be, for example, a flat shape, a curved surface shape, or any three-dimensional shape, and may be in a form of a film, a sheet, a plate, a foam, woven fabric, knitted fabric, a net, or nonwoven fabric. These can be used alone or in combination of two or more thereof.

The thickness of the substrate sheet can be, for example, about 5 μm or greater, about 15 μm or greater, or about 25 μm or greater, and can be about 300 μm or less, about 200 μm or less, or about 150 μm or less.

In the present disclosure, the bonding agent layer is intended to be a layer having adhesiveness different from the adhesiveness of the adhesive agent layer. Examples of a material of such a bonding agent layer include commonly used (meth)acrylic, polyolefin, polyurethane, polyester, and rubber bonding agents of a solvent type, an emulsion type, a pressure-sensitive type, a heat sensitive type, a thermosetting type, or a UV-curable type, and these can be used alone or in combination of two or more thereof. The bonding agent layer may be in a form of a double-sided adhesive tape.

The thickness of the bonding agent layer can be, for example, about 1 µm or greater, about 10 µm or greater, or about 30 µm or greater, and can be about 500 µm or less, about 300 µm or less, or about 100 µm or less.

Examples of the release liner can include paper; a resin material such as polyolefin such as polyethylene and polypropylene, polyester and cellulose acetate; and paper coated with such a resin material. These can be used alone or in combination of two or more thereof. These release liners may have surfaces release-treated with silicone or the like.

The thickness of the release liner can be about 5 µm or greater, about 15 µm or greater, or about 25 µm or greater, and can be about 300 µm or less, about 200 µm or less, or about 150 µm or less.

The medical member of the present disclosure is applied to skin. Such skin may be of either human or animal. Here, the skin in the present disclosure can also include a fingernail.

A method for producing the medical member of the present disclosure is not particularly limited. As an example, the method for producing the medical member of the present disclosure will be described below.

For example, polymerization means such as a solventless polymerization method is used to prepare a (meth)acrylate polymer by polymerizing a monomer component including the above-described monofunctional monomer and optionally a polyfunctional (meth)acrylate. The obtained (meth)acrylate polymer, a wettability stabilizer, and a crosslinking agent are mixed to prepare a mixture. The obtained mixture is applied to a substrate by using a known method such as a coating method to form an adhesive agent layer, followed by a drying step as necessary. Here, the adhesive agent layer can be applied to one or both sides of the substrate and may be applied to the entire surface or may be applied to a portion of the substrate. Then, heat or UV rays are applied directly or through a release liner to the obtained adhesive agent layer, and a cohesive tape can be obtained. When heat or UV rays are directly applied to the adhesive agent layer, a release liner may subsequently further be applied to the adhesive agent layer. The cohesive tape may be rolled up into a roll or may be cut into an appropriate size to form a sheet.

The medical member of the present disclosure can be formed by cutting the cohesive tape into a predetermined size, applying a bonding agent layer such as a double-sided adhesive tape to the substrate surface of the cohesive tape or one surface of a medical implement, and bonding the cut cohesive tape and the medical implement together via such a bonding agent layer.

The medical member of the present disclosure can be subjected to sterilization treatment with radiation such as gamma rays and electron beams. Among these, sterilization treatment by electron beams is preferable from the perspective of simplicity of facilities, productivity, and the like. The sterilization treatment may be performed, for example, separately on the cohesive tape, the medical implement, and the like, or may be performed on the configuration of the medical member. The sterilization treatment may be performed in batch or may be performed continuously but is preferably performed continuously from the perspective of productivity and the like.

An irradiation dose of radiation in the sterilization treatment is not particularly limited. For example, the irradiation dose can be about 10 kGy or greater, about 15 kGy or greater, or about 20 kGy or greater, and can be about 120 kGy or less, about 100 kGy or less, or about 80 kGy or less.

EXAMPLES

Specific embodiments of the present disclosure will be exemplified in the following examples, but the present invention is not limited to these embodiments.

Components used in the present examples are shown in Table 1 below.

TABLE 1

| Components | Abbreviation or trade name | Provider |
| --- | --- | --- |
| 2-ethylhexyl acrylate | 2EHA | BASF (U.S.) |
| Acrylic acid | AA | BASF (U.S.) |
| 1-hydroxycyclophenylketone | Omnirad 184 | IGM Resins USA Inc. (U.S.) |
| Acryloxybenzophenone | ABP | 3M (Minnesota, U.S.) |
| Hydrogenated rosin ester | Pinecrystal KE-311 | ARAKAWA CHEMICAL INDUSTRIES, LTD. (Chuo-ku, Osaka, Japan) |
| Rosin ester | Ester Gum 105 | ARAKAWA CHEMICAL INDUSTRIES, LTD. (Chuo-ku, Osaka, Japan) |
| Hydrogenated rosin ester | Pinecrystal KE-359 | ARAKAWA CHEMICAL INDUSTRIES, LTD. (Chuo-ku, Osaka, Japan) |
| Hydrogenated terpene phenol | YS Polystar (trade name) UH115 | YASUHARA CHEMICAL CO., LTD. (Fuchu-shi, Hiroshima, Japan) |
| Terpene phenol | YS Polystar (trade name) U115 | YASUHARA CHEMICAL CO., LTD. (Fuchu-shi, Hiroshima, Japan) |
| Hydrogenated petroleum resin | Alcon (trade name) M100 | ARAKAWA CHEMICAL INDUSTRIES, LTD. (Chuo-ku, Osaka, Japan) |
| Aliphatic hydrocarbon | Wingtack (trade name) Plus | Cray Valley Inc. (Pennsylvania, U.S.) |

Evaluation of a loss tangent (tan δ) and adhesive force of the adhesive agent layer was performed based on the use of various components such as the presence or absence of a wettability stabilizer.

Example 1

About 96.5 parts by mass of 2EHA, about 3.5 parts by mass of AA, about 0.2 parts by mass of Omnirad 184, and about 0.05 parts by mass of ABP were mixed and polymerized under solventless conditions. The obtained polymer was mixed with about 30 parts by mass of a wettability stabilizer KE-311 at 170° C., and an adhesive was prepared.

Example 2

An adhesive of Example 2 was prepared in the same manner as in Example 1, except that the wettability stabilizer was changed from KE-311 to 105.

Example 3

An adhesive of Example 3 was prepared in the same manner as in Example 1, except that the wettability stabilizer was changed from KE-311 to KE-359.

Example 4

An adhesive of Example 4 was prepared in the same manner as in Example 1, except that the wettability stabilizer was changed from KE-311 to YS Polystar (trade name) UH115.

Example 5

An adhesive of Example 5 was prepared in the same manner as in Example 1, except that the wettability stabilizer was changed from KE-311 to YS Polystar (trade name) U115.

Comparative Example 1

An adhesive of Comparative Example 1 was prepared in the same manner as in Example 1, except that no wettability stabilizer was used.

Comparative Example 2

An adhesive of Comparative Example 2 was prepared in the same manner as in Example 1, except that Alcon (trade name) M100 was used in place of KE-311.

Comparative Example 3

An adhesive of Comparative Example 3 was prepared in the same manner as in Example 1, except that Wingtack (trade name) Plus was used in place of KE-311.

Evaluation Test
Dynamic Viscoelasticity Measurement: Loss Tangent (Tan δ)

Advanced Rheometric Expansion System (ARES) available from Rheometric Scientific was used to determine the loss tangent (tan δ) at 90° C. of each adhesive sample after ultraviolet (UV) treatment at a frequency of 1 Hz and under a temperature rising condition of 5° C./min, and the loss tangent (tan δ) at 90° C. of each adhesive sample after UV treatment and then further sterilization treatment with electron beams (EB) (irradiation amount: about 75 kGy). The results are shown in Tables 2, 5 and FIG. 1. Here, FIG. 1 is a bar graph of an absolute value (|X−Y|) obtained by subtracting the loss tangent tan δ (Y) at 90° C. of the adhesive after UV irradiation treatment and then further electron beam sterilization treatment from the loss tangent tan δ (Y) at 90° C. of the adhesive after UV irradiation treatment; the smaller a value in the bar graph, the less the denaturation of wettability and the like of the adhesive after electron beam sterilization treatment.

Adhesive Force Test 1

The mixture made in the preparation of the adhesive was applied to a PET film having a thickness of 25 μm, and then irradiated with UV rays by an irradiation amount of about 50 mJ/cm$^2$ by using a metal halide lamp, and a cohesive tape including an adhesive agent layer having a thickness of about 90 μm.

The obtained cohesive tape was cut into a size of about 1 inch×about 6 inches, then the release liner was removed, and the adhesive agent layer of the cohesive tape was applied to a polypropylene plate (available from Standard Test Piece Inc., polypropylene (double-sided SG)) to prepare a test piece. The obtained test piece was attached to a tensile tester (available from A&D Company, Limited RTG-1250). The test piece was pulled at an angle of 180 degrees and speed of about 300 mm/minute with respect to the polypropylene plate to measure the adhesive force of the adhesive agent layer. The results are shown in Tables 3 and 5.

Here, "after UV treatment (a)" in the table refers to the adhesive force of the cohesive tape after UV irradiation treatment, and "after EB treatment (b)" refers to the adhesive force of the cohesive tape after UV irradiation treatment and then further electron beam sterilization treatment (irradiation amount: about 75 kGy), and "|a−b|" refers to an absolute value obtained by subtracting the adhesive force of the cohesive tape after UV irradiation treatment and then further electron beam sterilization treatment from the adhesive force of the cohesive tape after UV irradiation treatment; the smaller such a value, the less the denaturation of the adhesive force of the adhesive in the cohesive tape after electron beam sterilization treatment. Additionally, a "retention rate (%)" is calculated by Formula 3 below, and shows how much the adhesive force of the cohesive tape after UV treatment is maintained after EB treatment:

$$\text{Retention rate (\%)}=(\text{adhesive force}(b) \text{ of cohesive tape after EB treatment/adhesive force of cohesive tape after UV treatment}(a))\times 100 \quad \text{Formula 3}$$

Adhesive Force Test 2

A cohesive tape was prepared in the same manner as in the adhesive force test 1 described above. After the obtained cohesive tape was cut into a size of about 1 inch×about 6 inches, the release liner was removed, and the adhesive agent layer of the cohesive tape was applied to artificial leather (PBZ13001 KAKI available from IDEATEX JAPAN Co, Ltd.) that mimics skin to prepare a test piece. Here, two types of test pieces were prepared: one type of test pieces obtained immediately after applying the adhesive agent layer to the artificial leather and the other type of test pieces obtained in two minutes after application to the artificial leather. Each obtained test piece was attached to a tensile tester (RTG-1250, available from A&D Company, Limited), and was pulled at an angle of 180 degrees with respect to the artificial leather at speed of about 300 mm/min, and the adhesive force of the adhesive agent layer was measured. The results are shown in Table 4.

TABLE 2

|  | Example 1 | Example 2 | Example 3 | Example 4 |
|---|---|---|---|---|
| Type of component | Hydrogenated rosin ester | Rosin ester | Hydrogenated rosin ester | Hydrogenated terpene phenol |
| Blending amount of component (mass %) | 30 | 30 | 30 | 30 |
| Loss tangent (tan δ) After UV treatment (X) | 1.47 | 1.46 | 1.42 | 1.18 |
| After EB treatment (Y) | 1.14 | 1.16 | 1.14 | 0.94 |
| \|X − Y\| | 0.33 | 0.30 | 0.28 | 0.24 |

|  | Example 5 | Comparative Example 1 | Comparative Example 2 | Comparative Example 3 |
|---|---|---|---|---|
| Type of component | Terpene phenol | — | Hydrogenated petroleum resin | Aliphatic hydrocarbons |
| Blending amount of component (mass %) | 30 | 0 | 30 | 30 |
| Loss tangent (tan δ) After UV treatment (X) | 1.20 | 0.92 | 1.44 | 1.54 |
| After EB treatment (Y) | 0.97 | 0.33 | 0.92 | 0.97 |
| \|X − Y\| | 0.23 | 0.59 | 0.52 | 0.57 |

TABLE 3

|  | Example 4 | Example 5 | Comparative Example 1 |
|---|---|---|---|
| Type of component | Hydrogenated terpene phenol | Terpene phenol | — |
| Blending amount of component (mass %) | 30 | 30 | 0 |
| Adhesive force 1 (to PP plate) (N/inch) After UV treatment (a) | 10.2 | 9.5 | 14.0 |
| After EB treatment (b) | 9.4 | 8.8 | 5.4 |
| \|a − b\| | 0.8 | 0.7 | 8.6 |
| Retention rate (%) | 92.1 | 92.6 | 38.6 |

TABLE 4

|  |  | Example 5 | Comparative Example 1 |
|---|---|---|---|
| Type of component |  | Terpene phenol | — |
| Blending amount of component (mass %) |  | 30 | 0 |
| Adhesive force 2 (to artificial leather) (N/inch) | Immediately after After UV treatment (a) | 3.7 | 4.5 |
|  | After EB treatment (b) | 2.8 | 1.7 |
|  | \|a − b\| | 0.9 | 2.8 |
|  | Retention rate (%) | 75.7 | 37.8 |
|  | After 2 minutes After UV treatment (a) | 8.0 | 7.8 |
|  | After EB treatment (b) | 6.4 | 1.9 |
|  | \|a − b\| | 1.6 | 5.9 |
|  | Retention rate (%) | 80.0 | 24.4 |

The loss tangent (tan δ) and the adhesive force of the adhesive agent layer were evaluated based on the blending amount of terpene phenol that is a wettability stabilizer.

Comparative Example 4

An adhesive and a cohesive tape of Comparative Example 4 were prepared in the same manner as in Example 5, except that the blending amount of YS Polystar (trade name) U 115 was changed from 30 parts by mass to 5 parts by mass.

Comparative Example 5

An adhesive and a cohesive tape of Comparative Example 5 were prepared in the same manner as in Example 5, except that the blending amount of YS Polystar (trade name) U 115 was changed from 30 parts by mass to 10 parts by mass.

Example 6

An adhesive and a cohesive tape of Example 6 were prepared in the same manner as in Example 5, except that the blending amount of the YS Polystar (trade name) U 115 was changed from 30 parts by mass to 20 parts by mass.

Example 7

An adhesive and a cohesive tape of Example 7 were prepared in the same manner as in Example 5, except that the blending amount of YS Polystar (trade name) U 115 was changed from 30 parts by mass to 40 parts by mass.

Example 8

An adhesive and a cohesive tape of Example 8 were prepared in the same manner as in Example 5, except that the blending amount of YS Polystar (trade name) U 115 was changed from 30 parts by mass to 50 parts by mass.

As for the adhesives and the cohesive tapes in Examples 6 to 8 and Comparative Examples 4 and 5, the loss tangent and the adhesive force of the adhesive agent layer were evaluated in the same manner as described above. The results of Example 5 are shown in Table 5.

TABLE 5

| | | Comparative Example 4 | Comparative Example 5 | Example 6 | Example 5 | Example 7 | Example 8 |
|---|---|---|---|---|---|---|---|
| Type of component | | | | Terpene phenol | | | |
| Blending amount of component (mass %) | | 5 | 10 | 20 | 30 | 40 | 50 |
| Loss tangent (tan δ) | After UV treatment (X) | 0.99 | 1.10 | 1.16 | 1.20 | 1.03 | 1.10 |
| | After EB treatment (Y) | 0.41 | 0.54 | 0.80 | 0.97 | 0.93 | 1.07 |
| | |X − Y| | 0.58 | 0.56 | 0.36 | 0.22 | 0.10 | 0.03 |
| Adhesive force 1 (to PP plate) (N/inch) | After UV treatment (a) | 10.7 | 7.7 | 7.9 | 9.5 | 7.0 | 5.8 |
| | After EB treatment (b) | 13.7 | 9.7 | 7.7 | 8.8 | 8.1 | 5.1 |
| | |a − b| | 3.0 | 2.0 | 0.2 | 0.7 | 1.1 | 0.7 |

It is apparent to those skilled in the art that various modifications can be made to the embodiments and the examples described above without departing from the basic principles of the present invention. Additionally, it is apparent to those skilled in the art that various improvements and modifications of the present invention can be made without departing from the gist and the scope of the present invention.

What is claimed is:

1. A medical member for skin application comprising:
an adhesive agent layer resistant to radiation sterilization, the adhesive agent layer comprising:
a (meth)acrylic polymer having one or more UV crosslinkable site selected from a benzophenone group, a benzyl group, an o-benzoylbenzoate group, a thioxanthone group, a 3-ketocoumarin group, a 2-ethylanthraquinone group, and a camphor quinone group; and
a wettability stabilizer, wherein the wettability stabilizer is selected from a rosin ester resin, a terpene phenol resin, and hydrides thereof.

2. The medical member of claim 1, further comprising:
a medical implement.

3. The medical member of claim 2, wherein the medical implement is at least one selected from a backing, dosing equipment, communication equipment, testing equipment, and protective equipment.

4. The medical member of claim 1, wherein the wettability stabilizer is selected from a terpene phenol resin and a hydride thereof.

5. The medical member of claim 1, wherein the wettability stabilizer is present in an amount from 15 to 60 mass % with respect to the weight of the adhesive agent layer.

6. The medical member of claim 1, wherein the adhesive agent layer is a hot melt adhesive.

7. The medical member of claim 1, wherein a thickness of the adhesive agent layer is from 10 to 300 μm.

8. The medical member of claim 1, the (meth)acrylic polymer derived from:
one or more $C_{1-20}$alkyl (meth)acrylate monomer represented by one of formulae:

$CH_2=CH-COO-R^1$ or $CH_2=C(CH_3)-COO-R^1$, wherein: $R^1$ is a linear, branched, or cyclic alkyl group having from 1 to 20 carbon atoms;
one or more polar unsaturated monomer having a polar group and a vinylcarbonyl group characterized by a formula:

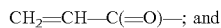
$CH_2=CH-C(=O)-$; and one or more (meth)acrylate monomer having a UV crosslinkable group selected from a benzophenone, a benzyl, an o-benzoylbenzoate, a thioxanthone, a 3-ketocoumarin, a 2-ethylanthraquinone, and a camphor quinone.

9. The medical member of claim 8, the one or more $C_{1-20}$alkyl (meth)acrylate monomer selected from methyl (meth)acrylate, ethyl (meth)acrylate, n-butyl (meth)acrylate, hexyl (meth)acrylate, n-octyl (meth)acrylate, 2-ethylhexyl (meth)acrylate, isobutyl (meth)acrylate, tert-butyl (meth)acrylate, cyclohexyl (meth)acrylate, isobornyl (meth)acrylate, and dicyclopentanyl (meth)acrylate.

10. The medical member of claim 8, the one or more polar unsaturated monomer selected from:
a hydroxyl group-containing unsaturated monomer selected from 2-hydroxyethyl (meth)acrylate, 3-hydroxypropyl (meth)acrylate, 4-hydroxybutyl (meth)acrylate, polyethylene glycol (meth)acrylate, and polypropylene glycol (meth)acrylate;
a carboxyl group-containing unsaturated monomer selected from acrylic acid, itaconic acid, maleic acid, and fumaric acid;
a carbamoyl group-containing unsaturated monomer selected from acrylamide;
an amino group-containing monomer selected from N,N-dimethylaminoethyl (meth)acrylate, N,N-diethylaminoethyl (meth)acrylate, and N,N-dimethylaminopropyl (meth)acrylate; and
an epoxy group-containing unsaturated monomer selected from glycidyl (meth)acrylate.

11. The medical member of claim 8, the one or more (meth)acrylate monomer having a UV crosslinkable group selected from 4-acryloyloxybenzophenone, 4-acryloyloxyethoxybenzophenone, 4-acryloyloxy-4'-methoxybenzophenone, 4-acryloyloxyethoxy-4'-methoxybenzophenone, 4-acryloyloxy-4'-bromobenzophenone, 4-acryloyloxyethoxy-4'-bromobenzophenone, 4-methacryloyloxybenzophenone, 4-methacryloyloxyethoxybenzophenone, 4-methacryloyloxy-4'-methoxybenzophenone, 4-methacryloyloxyethoxy-4'-methoxybenzophenone, 4-methacryloyloxy-4'-bromobenzophenone, and 4-methacryloyloxyethoxy-4'-bromobenzophenone.

12. The medical member of claim 8, the (meth)acrylic polymer derived from 2-ethylhexyl acrylate, acrylic acid, and acryloxybenzophenone.

13. The medical member of claim 12, the 2-ethylhexyl acrylate, acrylic acid, and acryloxybenzophenone present in a weight ratio of 96.5:3.5:0.5.

* * * * *